US010863890B2

(12) United States Patent
Lieponis

(10) Patent No.: US 10,863,890 B2
(45) Date of Patent: *Dec. 15, 2020

(54) MULTI-PURPOSE SURGICAL INSTRUMENT WITH REMOVABLE COMPONENT

(71) Applicant: Jonas V. Lieponis, Guilford, CT (US)

(72) Inventor: Jonas V. Lieponis, Guilford, CT (US)

(*) Notice: Subject to any disclaimer, the term of this patent is extended or adjusted under 35 U.S.C. 154(b) by 118 days.

This patent is subject to a terminal disclaimer.

(21) Appl. No.: 15/616,199

(22) Filed: Jun. 7, 2017

(65) Prior Publication Data

US 2017/0265728 A1  Sep. 21, 2017

Related U.S. Application Data

(63) Continuation of application No. 12/421,191, filed on Apr. 9, 2009, now Pat. No. 9,675,235, which is a continuation-in-part of application No. 11/757,707, filed on Jun. 4, 2007, now Pat. No. 7,842,027, which is a continuation-in-part of application No. 11/384,843, filed on Mar. 20, 2006, now abandoned.

(Continued)

(51) Int. Cl.
| | |
|---|---|
| *A61M 39/02* | (2006.01) |
| *A61B 1/015* | (2006.01) |
| *A61B 1/00* | (2006.01) |
| *A61M 1/00* | (2006.01) |
| *A61B 90/30* | (2016.01) |
| *A61M 27/00* | (2006.01) |
| *A61M 31/00* | (2006.01) |
| *A61M 29/00* | (2006.01) |

(52) U.S. Cl.
CPC .......... *A61B 1/015* (2013.01); *A61B 1/00105* (2013.01); *A61B 1/00165* (2013.01); *A61B 1/00167* (2013.01); *A61B 90/30* (2016.02); *A61M 1/008* (2013.01); *A61B 2090/306* (2016.02)

(58) Field of Classification Search
CPC ...... A61M 39/02; A61M 27/00; A61M 31/00; A61M 29/00
See application file for complete search history.

(56) References Cited

U.S. PATENT DOCUMENTS

| 3,261,356 A | 7/1966 | Wallace |
| 3,780,736 A | 12/1973 | Chen |

(Continued)

FOREIGN PATENT DOCUMENTS

EP  1 262 141 A1 * 10/1997

OTHER PUBLICATIONS

The American Heritage® Dictionary of the English Language, Fourth Edition, 2000.*

*Primary Examiner* — Tatyana Zalukaeva
*Assistant Examiner* — Ilya Y Treyger
(74) *Attorney, Agent, or Firm* — St. Onge Steward Johnston & Reens, LLC

(57) ABSTRACT

A combination aspiration/irrigation and illumination device using optical fibers circumferentially disposed around the aspiration conduit for transmitting illuminating light to a cavity to be aspirated. The aspiration conduit having a tip that is detachably affixed to and end of the aspiration conduit. The optical fibers terminated at a distance (d) from a distal end of the tip. Also provided is an image fiber(s) for transmitting image data from the distal end of the device.

13 Claims, 10 Drawing Sheets

Related U.S. Application Data

(60) Provisional application No. 60/663,690, filed on Mar. 21, 2005.

(56) References Cited

U.S. PATENT DOCUMENTS

| | | | |
|---|---|---|---|
| 3,916,948 A | | 11/1975 | Benjamin |
| 4,204,328 A | | 5/1980 | Kutner |
| 4,551,130 A | | 11/1985 | Herbert et al. |
| 4,617,013 A | | 10/1986 | Betz |
| 4,782,819 A | | 11/1988 | Adair |
| 4,872,837 A | | 10/1989 | Issalene et al. |
| 4,992,047 A | | 2/1991 | Warner |
| 5,026,367 A | | 6/1991 | Leckrone et al. |
| 5,201,730 A | | 4/1993 | Easley et al. |
| 5,207,648 A | * | 5/1993 | Gross ............... A61M 25/0014 604/164.09 |
| 5,213,092 A | | 5/1993 | Uram |
| 5,415,653 A | | 5/1995 | Wardle et al. |
| 5,588,952 A | | 12/1996 | Dandolu |
| 5,931,670 A | | 8/1999 | Davis |
| 6,007,776 A | | 12/1999 | Matsumoto |
| 6,283,961 B1 | * | 9/2001 | Underwood ...... A61M 25/0133 606/41 |
| 6,419,659 B1 | * | 7/2002 | Phelps ............... A61B 17/3478 604/164.01 |
| 6,572,578 B1 | | 6/2003 | Blanchard |
| 2003/0153897 A1 | | 8/2003 | Russo |

* cited by examiner

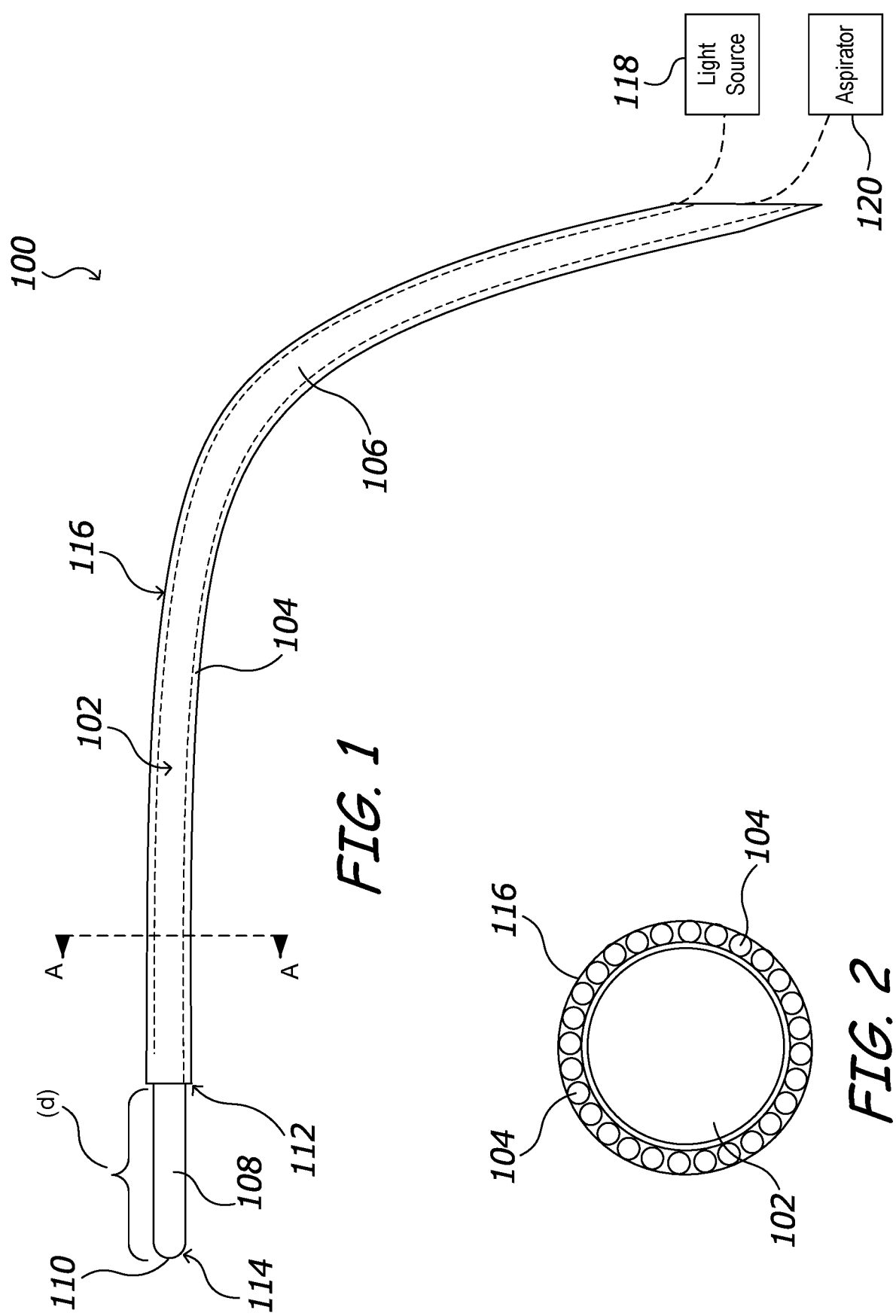

MULTI-PURPOSE SURGICAL INSTRUMENT WITH REMOVABLE COMPONENT

CROSS-REFERENCE TO RELATED APPLICATIONS

This application is a continuation-in-part of U.S. patent application Ser. No. 11/757,707 filed Jun. 4, 2007, which is a continuation-in-part of U.S. patent application Ser. No. 11/384,843 filed on Mar. 20, 2006, which claims the benefit of the filing date of U.S. Patent Application Ser. No. 60/663,690 filed Mar. 21, 2005.

FIELD OF THE INVENTION

This invention relates to a surgical instrument, more specifically this invention relates to a combination suction/irrigation device and optical device that may provide a visual indication of the area in which the tool is inserted.

BACKGROUND OF THE INVENTION

Minimally invasive surgery provides some significant advantages over open surgical procedures and as such, is being more frequently utilized. However, minimally invasive surgery and surgical techniques, for example, minimal incision surgery such as is utilized in spinal procedures, have created a special set of requirements with regard to the visualization of the operative field. These special requirements or changed parameters include the operative field being significantly reduced in size as compared to open surgical procedures. However, the depth parameter for the surgical procedure has remained unchanged. Therefore, the incision size to incision depth ratio has been markedly decreased very often geometrically creating unique challenges for the surgeon.

For example, unique geometry of the reduced size of the incision places severe constraints on the space available for the placement of surgical instruments in the area where the procedure is being performed. Visualization of the surgical area is also severely limited due to among other things, the size of the incision. As such, the size and number of surgical instruments that may be simultaneously used during minimally invasive surgical procedures is quite limited.

Additionally, minimally invasive surgical techniques typically require suction to be placed or located almost directly adjacent to the operative site. The proximity of the suction and visualization devices creates additional challenges relating to: design and material choice, and cost of manufacture/purchase. For example, especially when performing procedures with relatively small space constraints such as for example minimally invasive surgery, frequently requires the surgeon to utilize relatively high-speed abrasive rotating instruments. With relatively tight space constraints, this type of cutting tool may frequently come into contact with other surgical devices positioned within the surgical area. It is not uncommon for the other surgical devices to become damaged by this incidental contact. This can become quite costly for the hospital/surgeon to have to regularly repair and/or replace expensive surgical equipment in this manner.

Another problem with know illumination systems is the generation of heat at the light exit location due to the relatively large amount of optical energy exiting the device. Excessive heat in a surgical area should be avoided as it can lead to congealing of blood and in certain cases, burning of the surrounding tissue.

A number of previous systems have attempted to address a few of these problems with limited success. For example, U.S. Pat. No. 5,588,952 ("Dandolu") discloses a combination illumination and aspiration device. Dandolu further discloses that "reflector" is positioned at the tip of the device to diffuse and focus the emitted light from the side wall of the device. However, Dandolu fails to teach or suggest a system that projects illuminating light ahead of the suction tip. Rather, Dandolu discloses that a fiber optic cable emits light out of a side portion of the device, perpendicular to the longitudinal axis of the suction device. Additionally, Dandolu concentrates the optical exit point of the illuminating light thereby generating excessive heat, which is highly undesirable.

U.S. Pat. No. 4,872,837 ("Issalene et al.") discloses an instrument capable of both illumination and aspiration. Issalene et al. further teaches use of a cannula having a beveled front end that may be used to concentrate and/or direct illuminating light in a controlled manner. However, Issalene et al. fails to teach or suggest a system that includes a plurality of optical fibers surrounding an aspiration tube to maximize the light projected ahead of the suction tip or that the optical fibers terminate a distance from the tip such that in the event of damage to the tip, the optical fibers are not damaged. Additionally, Issalene et al. provides a single optical point of illumination that will generate excessive heat.

U.S. Pat. No. 5,213,092 ("Uram") discloses a combination aspiration and illumination/image guiding system. However, Uram positions the illuminating/image guides and aspiration tube side-by-side, which disadvantageously increases the overall size of the device. With minimally invasive surgical procedures, it is critical that the device remain a small in diameter as reasonably possible. Accordingly, Uram fails to teach a combination suction and illumination device that presents one concentric system to provide the smallest diameter possible. In addition, as the illumination guide is offset from the suction tube, such that illumination of the area ahead of the device will suffer.

Therefore, what is desired is a surgical system and method that provides for increased visualization in the surgical area while at the same time not further restricting the working area for the surgeon.

It is further desired to provide a surgical system and method that may effectively be utilized in connection with minimally invasive surgery that provides for increased visualization of the area where the surgical procedure is to be performed.

It is still further desired to provide a surgical system and method that minimizes the number of surgical tools that must be simultaneously inserted into the incision.

It is yet further desired to provide a surgical system and method that reduces the costs of suction and visualization tools.

It is also desired to provide a surgical system that allows the user to position the device in various angles and locations despite having limited access to the area as is the case in non-invasive surgical procedures.

It is further desired to provide a surgical system and method that provides illuminating light to a surgical area while minimizing any amount of heat that may be generated by the illuminating light.

SUMMARY OF THE INVENTION

These and other objectives are achieved by provision of a surgical device that combines the applications of visualization and suction into a single instrument. Illuminating light is transmitted down the length of the device by means of optical fibers, which are concentrically positioned around an aspiration tube. The optical fibers are terminated at a distance from the tip of the device, which may be provided as a transparent, translucent or opaque material.

Additionally, in one advantageous embodiment, the optical fibers are machined at an angle relative to the longitudinal axis of the optical fiber to increase illumination of a particular area. In one advantageous embodiment, the angle may range from about 45° to about 70° from the longitudinal axis. Still further, it is contemplated that multiple optical fibers with angled ends may be provided to concentrate the light inwardly with respect to the suction tube to provide increased illumination to an area ahead of the tip of the device.

For this application the following terms and definitions shall apply:

The term "network" as used herein includes both networks and internetworks of all kinds, including the Internet, and is not limited to any particular network or inter-network.

The terms "coupled", "coupled to", and "coupled with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The combined visualization and suction device provides a number of significant advantages over previous systems. For example, in minimally invasive surgery, the incision size is greatly reduced but the depth of the incision remains constant with open surgical procedures. This means the angle at which the surgical instruments enter and are placed in the procedure area is relatively large (i.e., approaching perpendicular). Therefore, the fewer instruments simultaneously inserted into the incision and the smaller in diameter each instrument, the greater flexibility the surgeon has to manipulate the surgical instruments.

The combination of suction and visualization instruments into one surgical device provides the distinct advantage of alleviating space constraints for the surgeon, especially is this so when the outside diameter (OD) of the combination instrument is essentially the same size as a suction only tool or perhaps only marginally larger.

In another advantageous embodiment, the suction tip of the combination device is provided made of a transparent or translucent material such that visual obstruction to the work area is minimized. The configuration of the fiber optic strands may be selected such that they may be used to effectively illuminate the work area while not providing an obstruction to visualization.

In still another advantageous embodiment, the optical fibers may be positioned such that the illuminating light is focused inward, toward a point located ahead of the tip of the tip. Optical fibers that are cut at a 90 degree angle or perpendicular to the longitudinal axis of the optical fiber, typically permit the light to exit the end of the fiber in a random fashion due to the inherently random reflection and refraction of the light propagating in the optical fiber. However, it is contemplated the exit ends of the optical fibers may be cut or machined at an angle relative to the longitudinal axis so as to direct the light to the shorter side of the oblique fiber end. In one advantageous embodiment, the cut or machined angle end may range from about 70 degrees to about 45 degrees.

Advantageously, the optical fibers may be positioned about the circumference of the suction tube in such a manner as to focus the illuminating light inward toward the center of the visual field directly ahead of the tip. To accomplish this, the optical fibers may be positioned with the oblique ends of the optical fibers facing inward toward the visual field.

To achieve uniformity of angle in the various optical fibers, the optical fibers may be cut or machined by adhering the optical fibers to a sheet of material and then cutting or machining the ends at a uniform angle. The optical fibers may then be applied or adhered to a suction cannula providing all of the fibers at a uniform orientation facing toward the visualization field to maximize illumination.

It is further conceived that the combination surgical device be kept as inexpensive to manufacture as reasonably possible such that incidental contact and damage caused to the combination surgical device will not greatly impact operating costs. To accomplish this, the combination surgical tool may be provided as a disposable device providing for reduced costs.

Another problem faced by surgeons in tight operating environments is that when a relatively high-speed abrasive rotating instrument comes into contact with another surgical tools, particles can be produced, which cannot subsequently be removed from the surgical area. This is especially undesirable if the particles are metallic because they may produce artifacts on post-operative imaging studies. Therefore, it is further contemplated that in one embodiment the combination surgical device may be made from non-metallic materials. In other embodiments, the combination surgical device may comprise a metallic material or alloy.

While the invention has been thus far focused on providing the combination of a suction and illuminating surgical device, it is further contemplated that the device may yet further be provided with coherent optical fibers for receiving reflected light to be transmitted to the surgeon. This reflected light may be provided directly to the surgeon via, for example, an eye piece, or may be transmitted to a camera, which may then generate a video signal representative of the area ahead of the suction tip. In this manner the combination surgical device may fully serve as the suction and visualization device.

In one advantageous embodiment, a medical instrument for providing illuminating light to and aspiration of a cavity is provided comprising an aspiration conduit coupled to an aspirator for aspirating fluid and particles from the cavity, the aspiration conduit having a distal end with a concave tip. The instrument further comprises a plurality of optical fibers coupled to a light source and circumferentially positioned about the aspiration conduit for transmitting illuminating light to the cavity, the plurality of optical fibers extending along a length of the aspiration conduit. The instrument is provided such that the optical fibers are provided with distal ends having an angled surface relative to a longitudinal axis of the aspiration conduit such that the illuminating light transmitted by the optical fibers is directed radially inward relative to the aspiration conduit.

In another advantageous embodiment, a medical instrument for providing illuminating light to and aspiration of a cavity is provided comprising an aspiration conduit for aspirating fluid and particles from the cavity, a valve coupled to the aspiration conduit, an aspirator coupled to the valve, a fluid source coupled to the valve and a switch connected to the valve. The instrument is provided such that the valve may selectively be switched to fluidly couple between the aspirator and the aspiration conduit or the fluid source and the aspiration conduit. The instrument further comprises a plurality of optical fibers coupled to a light source and circumferentially positioned about the aspiration conduit for transmitting illuminating light to the cavity.

In still another advantageous embodiment, a method for selectively clearing a clogged combination illumination/aspiration medical instrument is provided comprising the steps of coupling an aspiration conduit to a valve, coupling an aspirator to the valve and coupling a fluid source to the valve. The method further comprises the steps of selectively aspirating a cavity and clearing the device by switching the valve to couple between the aspiration conduit and the aspirator or the aspiration conduit and the fluid source. Finally, the method comprises the steps of positioning a plurality of optical fibers circumferentially about the aspiration conduit and illuminating an area ahead of a distal end of the optical fibers.

In a further advantageous embodiment, a medical instrument for providing illuminating light to and aspiration of a cavity is provided comprising an aspiration conduit coupled to an aspirator for aspirating fluid and particles from the cavity, the aspiration conduit having a distal end and a detachable tip affixed to the distal end. The medical instrument further comprises a plurality of optical fibers coupled to a light source and circumferentially positioned about the aspiration conduit for transmitting illuminating light to the cavity, the plurality of optical fibers extending along a length of the aspiration conduit.

In another advantageous embodiment, a medical instrument for providing illuminating light to and aspiration of a cavity is provided where the device comprises an aspiration conduit coupled to an aspirator for aspirating fluid and particles from the cavity, the aspiration conduit having a distal end. The medical instrument further comprises a sheath enclosing a plurality of optical fibers, the plurality of optical fibers positioned circumferentially about a cavity located along a longitudinal axis of the sheath. The optical fibers have distal ends from which illuminating light exits. The medical instrument also comprises a light source coupled to proximal ends of the plurality of optical fibers. The medical instrument is provided such that the aspiration conduit is insertable into the cavity so that the distal end of the aspiration conduit is adjustable relative to the distal ends of the plurality of optical fibers.

In still another advantageous embodiment, the medical instrument is further provided with a locking device to lock the aspiration conduit in a position relative to the distal ends of the optical fibers.

Other objects of the invention and its particular features and advantages will become more apparent from consideration of the following drawings and accompanying detailed description.

BRIEF DESCRIPTION OF THE DRAWINGS

FIG. 1 is an illustration of one advantageous embodiment of the present invention.

FIG. 2 is a cross-sectional view along line AA according to FIG. 1.

DETAILED DESCRIPTION OF THE INVENTION

Figure 3:
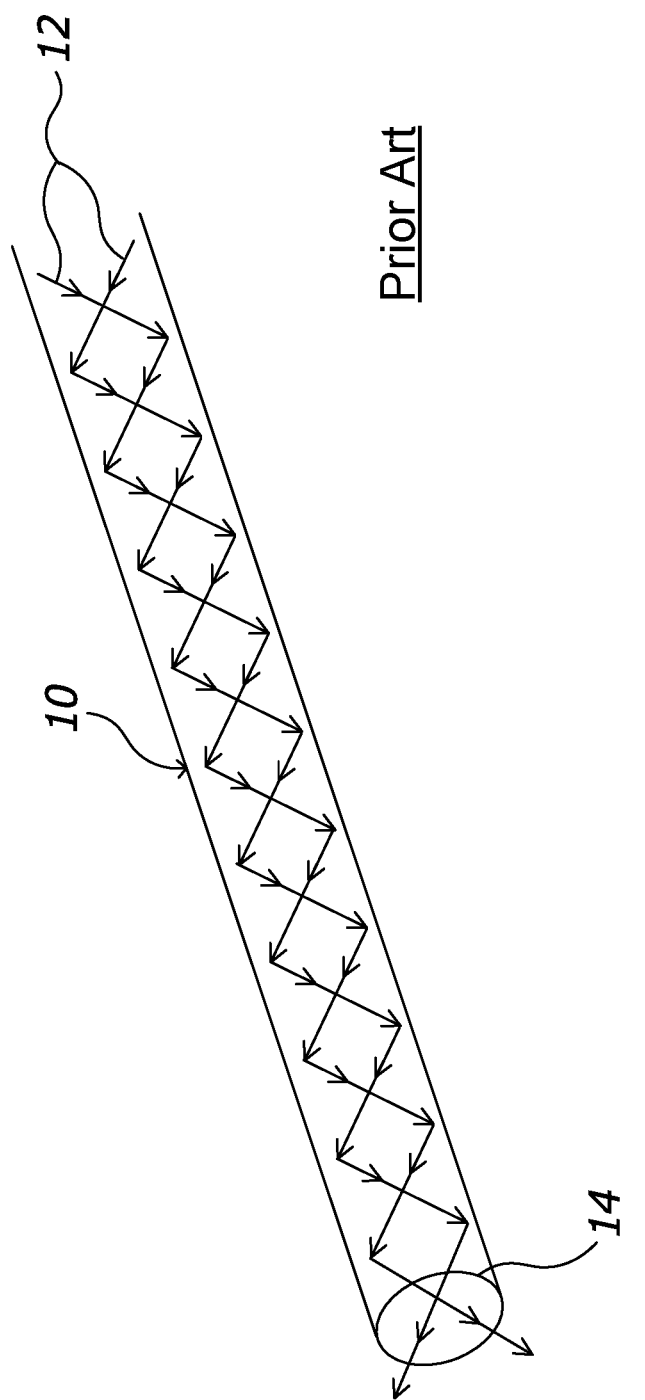
FIG. 3 is an illustration of an optical fiber with an end cut or machined at a nominal 90° angle.

Referring now to the drawings, wherein like reference numerals designate corresponding structure throughout the views.

FIG. 1 depicts aspiration and illumination device 100 according to one advantageous aspect of the present invention. Aspiration and illumination device 100 generally comprises aspiration conduit 102 and optical fibers 104. As illustrated in FIG. 2 along section line AA, optical fibers 104 are positioned circumferentially about aspiration conduit 102.

Aspiration conduit 102, in one advantageous embodiment, preferably comprises a non-metallic substance such as, for example, a flexible plastic material. It is further contemplated that aspiration conduit 102 may be provided of a material that can hold a shape when deformed providing increased control for the surgeon.

As can be seen in FIG. 1, aspiration conduit 102 comprises a body portion 106 and a tip 108, the tip 108 provided with a distal end 110. In one advantageous embodiment, tip 108 is provided as a transparent or at least, a translucent material, which will reduce any shadowing that, may occur or obstruct the surgeon's view of the cavity (not shown). Tip 108 is provided with an opening therein to allow for the introduction of fluids and particles therein to provide aspiration of the cavity as desired. The rate of aspiration is controlled by the surgeon via means commonly used in the art.

It may further be noted from FIG. 1 that optical fibers 104 are terminated at a distance (d) from distal end 110. The ends 112 of optical fibers 104 are positioned circumferentially about tip 108. As tip 108 is provided as a transparent or translucent material, the illuminating light exiting ends 112 will not be impeded but can travel along a length of tip 108 and may even travel through a portion of tip 108 to illuminate the cavity (not shown).

It is further contemplated that distal end 110 may, in another advantageous embodiment, be provided with rounded contour edges 114, however, it is contemplated that many differing configurations may be utilized for distal end 110. It is still further contemplated that the distance (d) may be varied depending upon the application and use.

Still further provided is sheath 116, which is provided enclosing both aspiration conduit 102 and optical fibers 104. Sheath 116 may comprise virtually any desired material that can enclose and protect optical fibers 104 while still allowing deflection of aspiration and illumination device 100. As shown in FIG. 1, sheath 116 may in one advantageous embodiment, terminate at or near ends 112 of optical fibers 104 so as not to interfere with the illuminating light exiting optical fibers 104.

Also shown in FIG. 1 are light source 118 and aspirator 120. Light source 118 is provided to generate illuminating light that is coupled into optical fibers 104 for transmission to the cavity. Light source 118 may comprise, in one advantageous embodiment, a Light Emitting Diode(s) (LED). In addition, aspirator 120 is illustrated coupled to aspiration conduit 102. As previously discussed, the rate of aspiration is controlled by the surgeon and may comprise a pre-selected flow rate, a controlled variable flow rate and/or combinations thereof.

As can be seen from FIGS. 1 and 2, the diameter of aspiration and illumination device 100 is kept to a minimum as optical fibers 104 are closely positioned about aspiration conduit 102 and enclosed by a relatively thin sheath 116. This provides a distinct advantage over prior art devices. For example, in minimally invasive surgery, while the incision size is reduced, the depth of the incision remains constant with open surgical procedures. This means that the angle at which the surgical instruments enter and are placed in the procedure area is relatively large (i.e. the instruments are positioned almost straight up and down relative to the incision). Therefore, the smaller in diameter each instrument, the greater flexibility the surgeon has to manipulate the surgical instruments.

Referring now to FIG. 3, we see an optical fiber 10 as is known in the prior art. As illustrated, illuminating light 12 is coupled into optical fiber 10 in a known manner. The illuminating light 12 is transmitted down optical fiber 10 in a manner corresponding to the construction of the particular optical fiber 10. An end 14 of optical fiber 10 is shown formed as a 90° angle with respect to the longitudinal axis of optical fiber 10. As illustrated, the illuminating light 12 exiting end 14 exits in a scattered fashion providing a relatively wide illumination pattern.

Figure 4:
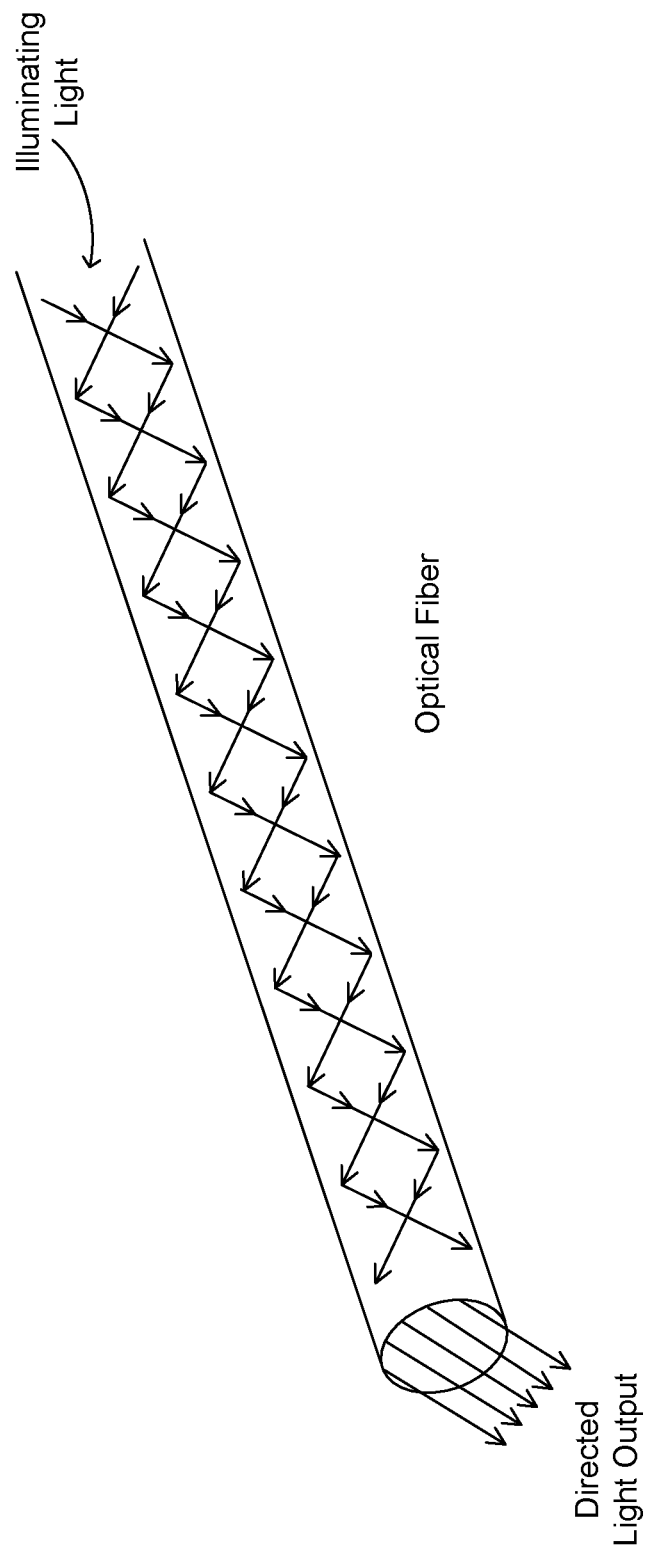
FIG. 4 is an illustration of an optical fiber according to FIG. 2 with an end cut or machined at an angle relative to the longitudinal axis of the optical fiber

Alternatively, turning now to FIG. 4 it can be seen that optical fiber 104, while similar to optical fiber 10, differs in that end 112 is formed at an angle relative to the longitudinal axis of optical fiber 104. In this manner, illuminating light, rather than exiting end 112 in a scattered fashion, is generally directed as indicated. In this manner, increased illumination of a particular area may be achieved. It should be noted that, while the light is shown exiting the end of the angled end 112 of the optical fiber 104 at a 45 degree angle relative to the longitudinal axis, it is contemplated that the end 112 may be shaped to a wide variety of angles (e.g. 45° to about 70° from the longitudinal axis) may be selected depending upon the application and procedure to be performed.

It should be noted that, while U.S. Pat. No. 4,872,837 ("Issalene et al.") discloses a cannula having a beveled front end that may be used to concentrate and/or direct illuminating light in a somewhat controlled manner, Issalene et al. fails to teach a device that can concentrate illuminating light in front of an aspirating tube.

Figure 5:
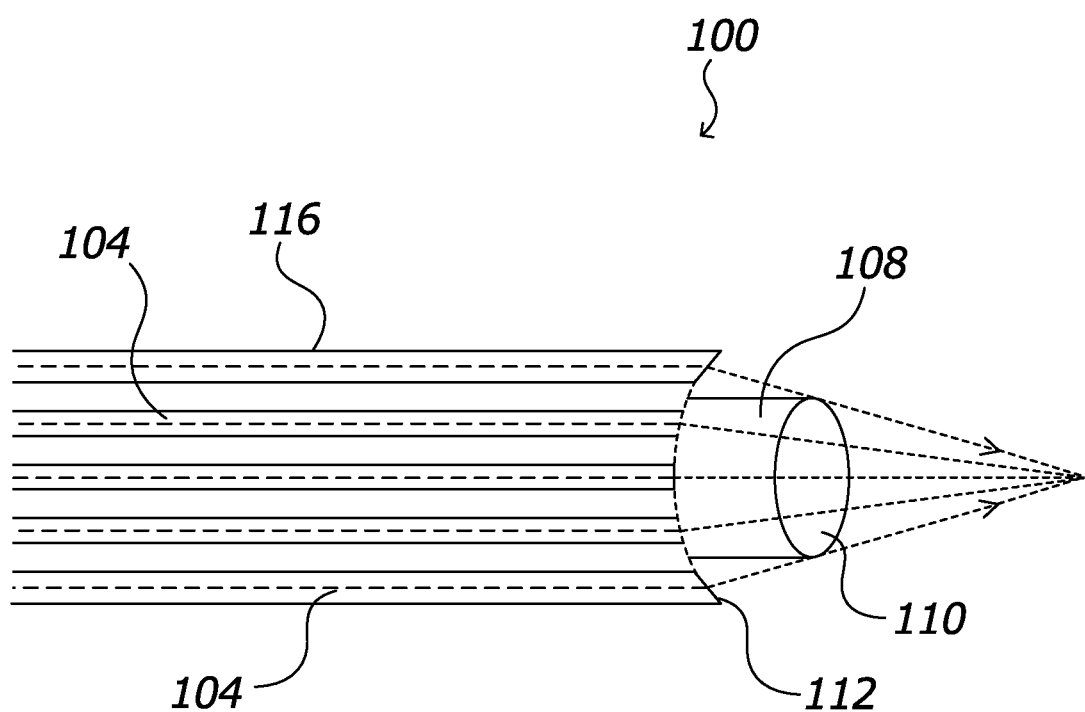
FIG. 5 is an illustration according to FIG. 2 of the optical fibers transmitting illuminating light to a point ahead of the tip of the device.

This is illustrated in FIG. 5. For example, aspiration and illumination device 100 is shown with the ends 112 of optical fiber 104 having beveled edges. In this advantageous embodiment, the illuminating light that exits ends 112 is directed inward relative to aspiration conduit 102. The optical fibers 104 are concentrically positioned about aspiration conduit 102 and are positioned such that the beveled ends 112 all face inward. In this manner, the directed light focuses at a point ahead of distal end 110 providing for increased light output in the cavity for the surgeon.

Again, the distal end may be provided as a transparent or translucent material to prevent interference with the light output and distal end 110 may be provided with as either a flat end or with a rounded contour. Sheath 116 is shown terminating prior to beveled ends 112 so as not to interfere with the illuminating light exiting therefrom.

Figure 6:
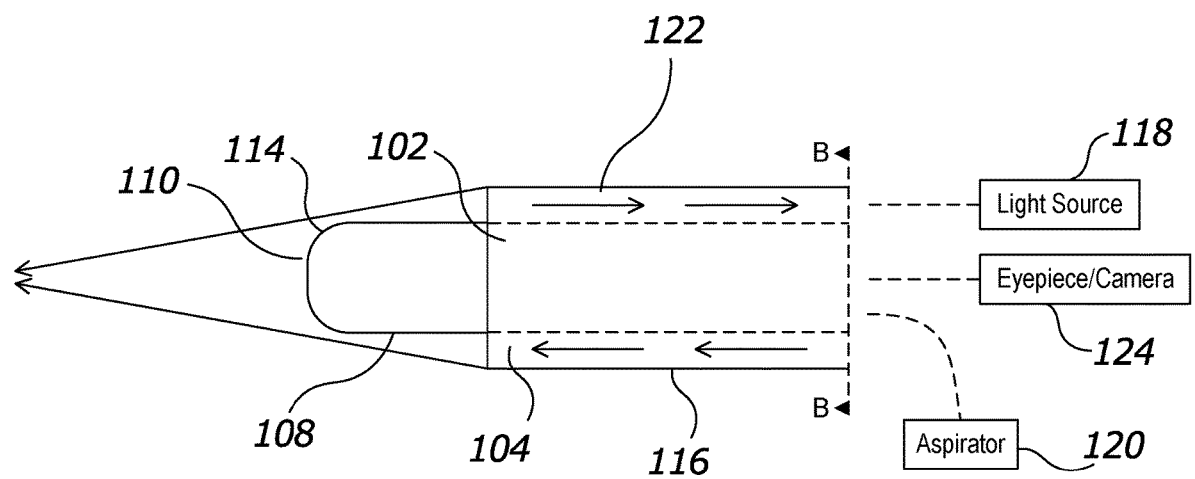
FIG. 6 is an illustration of another advantageous embodiment of the present invention.
Figure 7:
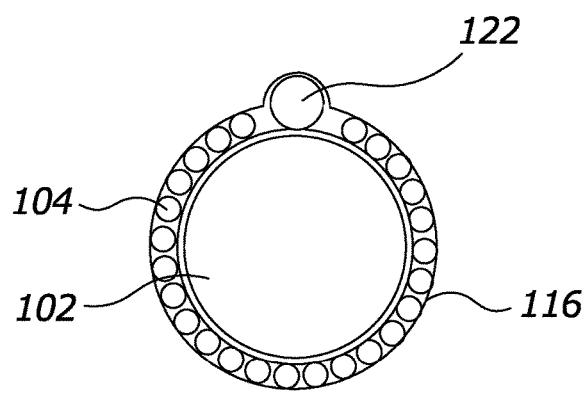
FIG. 7 is a cross-sectional view along line BB according to FIG. 6.

Turning now to FIGS. 6 and 7 we see an alternative embodiment of the present invention illustrated. This embodiment is similar in operation as that illustrated in connection with FIGS. 1 and 2 except, that image optical fiber(s) 122 is illustrated adjacent to the optical fibers 104. This can be seen with reference to FIG. 7, which is a cross-sectional view taken along line BB in FIG. 6. The entire device is encased in sheath 116 as previously described.

Image optical fibers 122 may comprise, for example, a single flexible optical fiber or may comprise coherent optical fibers that can pick up light reflected from the cavity and transmit the reflected light along image optical fiber(s) 122 back to an eyepiece or camera 124. In this manner, not only can the surgeon transmit illuminating light to the cavity with a combination aspiration and illumination device, but can further reduce the number of surgical tools in the incision by using the same tool to transmit image data. This may be especially effective where a camera is utilized and the surgeon is provided with a video display (not shown) for viewing the surgical procedure.

Like the embodiment disclosed in FIGS. 1 and 2, it is contemplated that the device including the image optical fiber may also be flexible and hold a shape upon deformation. Further, the device may comprise non-metallic compositions and be of a disposable nature. In this manner, accidental contact with, for example, rotating cutting devices will not result in metallic particles being left in the cavity or require sterilization.

The combination aspiration and illumination device then provides a relatively small compact device for the surgeon, which reduces the number and size of tools used during minimally invasive surgical procedures. In addition, the disposable device allows for increased flexibility of use and is cost effective.

Figure 8:
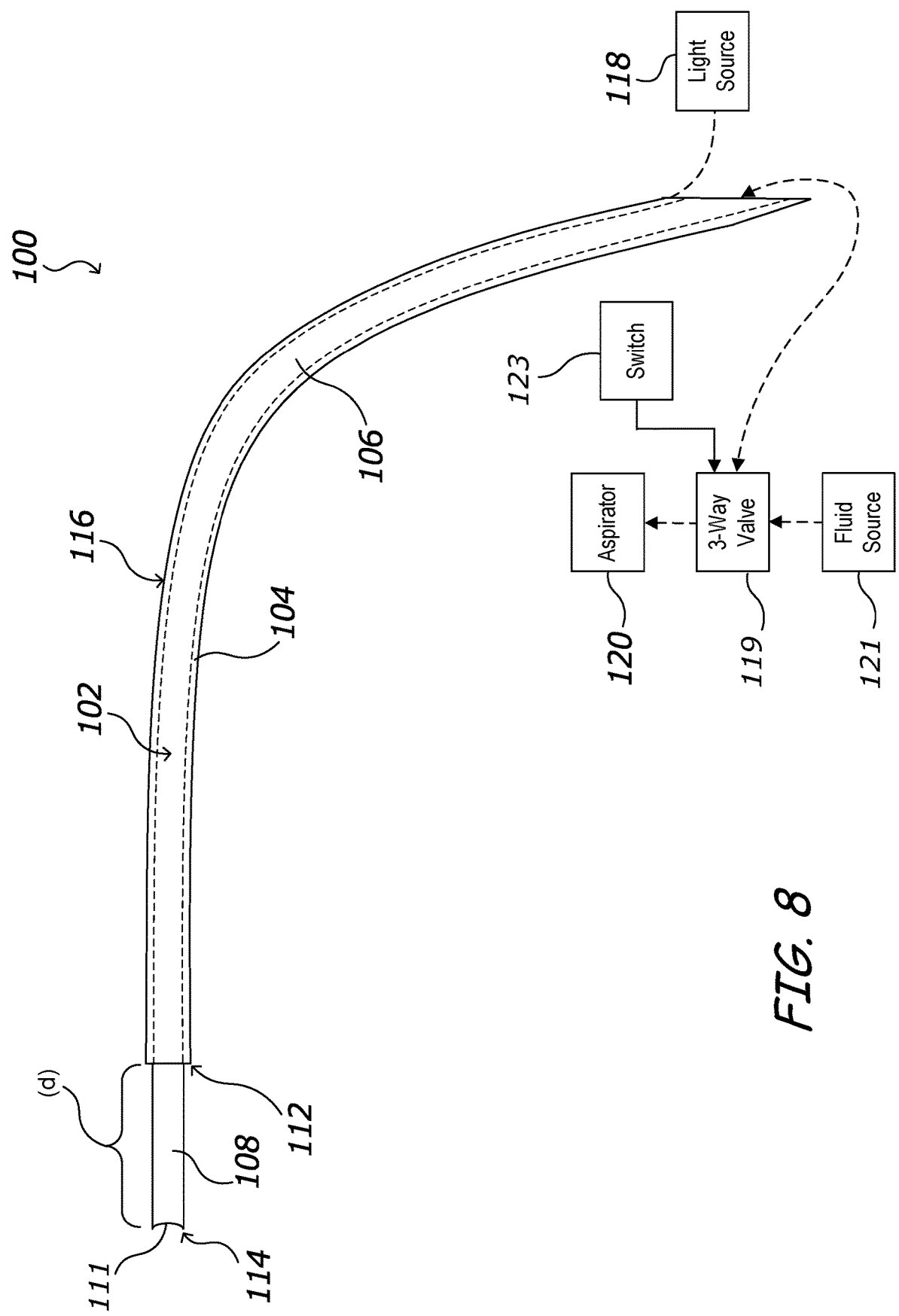
FIG. 8 is an illustration of another advantageous embodiment of the present invention.

Referring now to FIG. 8, an alternative embodiment for the configuration of tip 108 is provided. In this embodiment, tip 108 is provided with distal end 110 that is provided as a concave end 111 rather than the rounded contour edges as depicted in FIG. 1. This provides that distinct advantage of providing a multi-purpose tool for the surgeon when, for example, the surgeon is suturing an area. This is because the concave end can be used to hold it down while the surgeon is completing the suture. The concave surface will act to maintain the suture on the concave end 111 while the suture is tied off.

It is contemplated that tip 108 in this embodiment may again be provided as a transparent or translucent material as described in connection with FIG. 1.

Also illustrated in FIG. 8 is 3-way valve 119, which is variously coupled to aspirator 120 and fluid source 121. In this advantageous embodiment, 3-way valve 119 is provided with a switch 123 that is operated by the physician to switch between "aspiration mode" in which the aspirator is fluidly coupled through 3-way valve 119 to aspiration conduit 102 and "irrigation mode" in which fluid source 121 is fluidly coupled through 3-way valve 119 to aspiration conduit 102. It is contemplated that aspiration conduit 102 may, at times, become either partially or fully clogged during a procedure. In order to clear the obstruction, the surgeon has the option to actuate switch 123 to switch 3-way valve 119 to "irrigation mode" where pressurized fluid from fluid source 121 is fed into aspiration conduit 102 to dislodge the obstruction.

It is contemplated that switch 123 may be located on 3-way valve 119, or may be located on aspiration and illumination device 100. The connection between switch 123 and 3-way valve 119 may comprise a hard-wired or a wireless connection. In addition, it is contemplated that the surgeon may, in still another embodiment, control the pressure of the fluid transmitted to aspiration conduit 102. In this manner, the surgeon may provide irrigation in an area where a procedure is being performed as desired and may then switch back to aspiration mode. Alternatively, the surgeon may remove aspiration and illumination device 100 from the area where a procedure is being performed in the event of an obstruction in aspiration conduit 102, and may blow the obstruction out via relatively high pressure fluid from fluid source 121.

Figure 9:
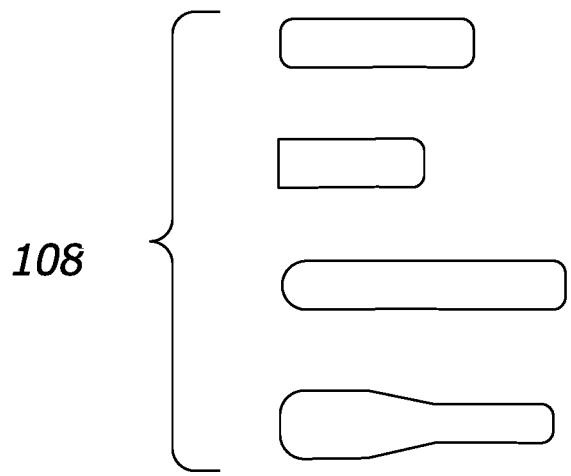
FIG. 9 is an illustration of various tip configurations that may be used with the aspiration and illumination device.

FIG. 9 is an illustration of various tips 108 provided for attachment to aspiration conduit 102 within aspiration and illumination device 100. It is contemplated that the various tips 108 may comprise many differing configurations, including, for example but not limited to, a concave or a convex tip configuration, various lengths, various shapes (cylinders, frusto-cones, paddle-shaped, etc.), and various diameters. It is further contemplated that the various tips 108 may be provided comprising various materials that may be selected depending upon the procedure and may include, for example, but not limited to, a clear or translucent plastic or polymer, a metal or alloy, an opaque material, a flexible or pliable material, or a rigid material. In any event, the particular tip 108 may be interchanged for any other tip 108 allowing for a more flexible system for the physician. The tips 108 may be provided as single or multiple use components, and may be provided as a packaged supply of various tips 108 or sold and supplied individually.

Figure 10:
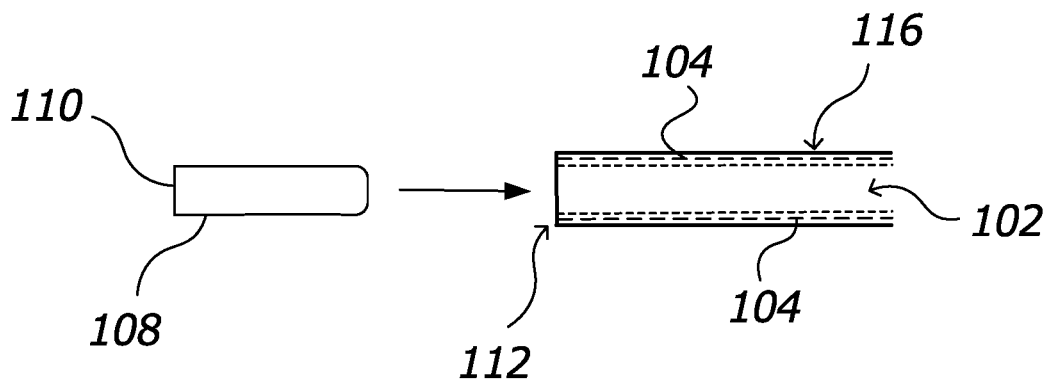
FIG. 10 is an illustration of a selected tip prior to attachment to the aspiration and illumination device.
Figure 11:
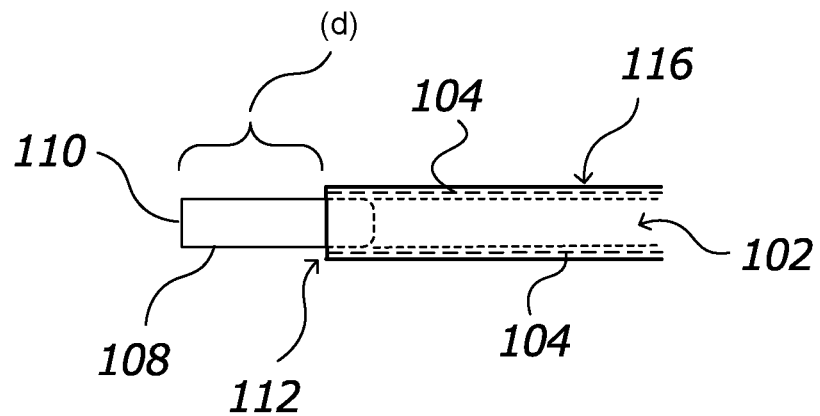
FIG. 11 is an illustration of the aspiration and illumination device according to FIG. 10 with the tip attached.

FIGS. 10 and 11 illustrate the attachment of a tip 108 to aspiration and illumination device 100. The tip 108 may be provided with an outer diameter that is marginally smaller than an inner diameter of aspiration conduit 102. The selected tip 108 may be provided as a friction fit having a slightly expanding diameter such that upon advancement of the tip 108 in aspiration conduit 102, the tip becomes firmly seated as is illustrated in FIG. 11. Alternatively, the tip 108 may be provided as a threaded or rotatable adapter that may be rotated into a secure position, such as, for example, a luer-type locking arrangement. For example, it is contemplated that the tip 108 may be rotated into a locked secure position and may be detached by reverse rotation of the tip 108.

The removable tip 108 provides greater versatility for the physician, but also provides for replacement of the tip 108 if it becomes damaged due to, for example, inadvertent contact with cutting equipment used in the surgical area. Additionally, the termination of the optical fibers 104 at a distance (d) from distal end 110 serves to protect the optical fibers 104 from inadvertent damage. The circumferential positioning of the fibers allows for increased illumination of the surgical area.

Figure 12:
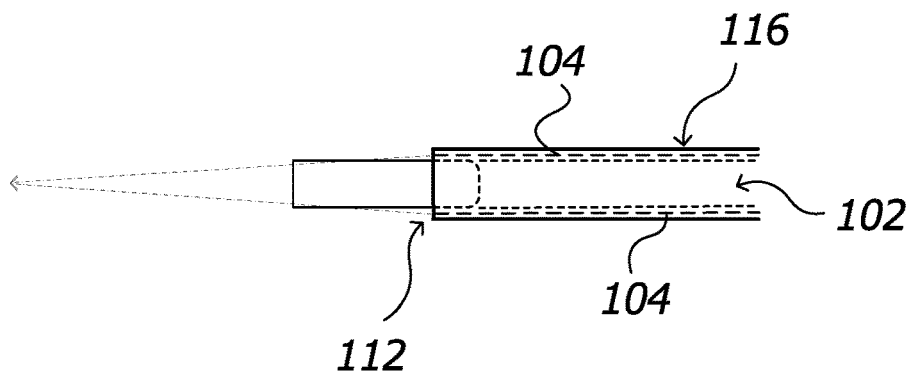
FIGS. 12-14 are illustrations of various embodiments according to FIG. 4.
Figure 13:
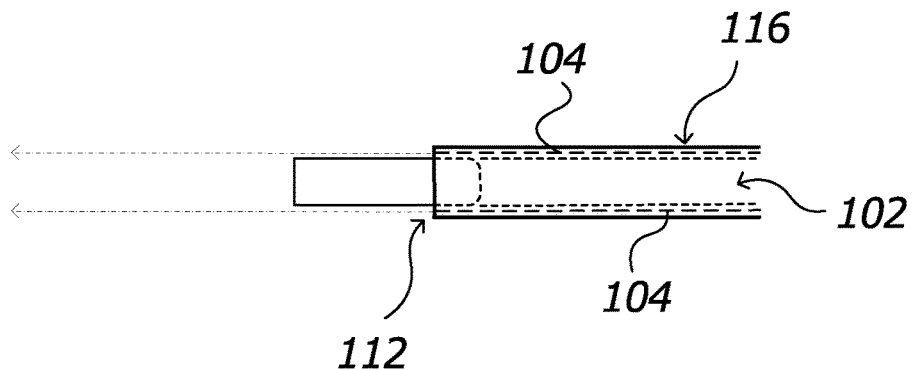
Figure 14:
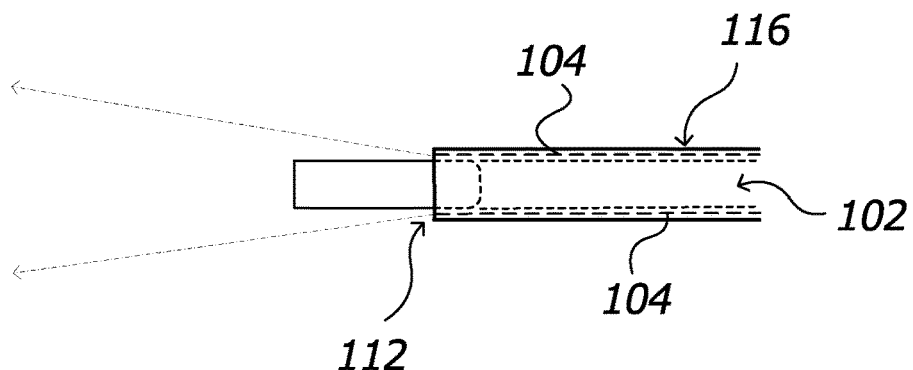

Referring now to FIGS. 12-14, it is contemplated that the ends of the optical fibers may be machined to direct the light exiting therefrom in virtually any direction desired. For example, the optical fibers may be machined at substantially a 90° angle relative to the longitudinal axis of the fiber or at an angle thereto. It is further contemplated that the angle could be provided so as to direct the illuminating light radially inward toward a point ahead of the tip 108, or to direct the light radially outward to broadly illuminate the surgical area.

Figure 15A:
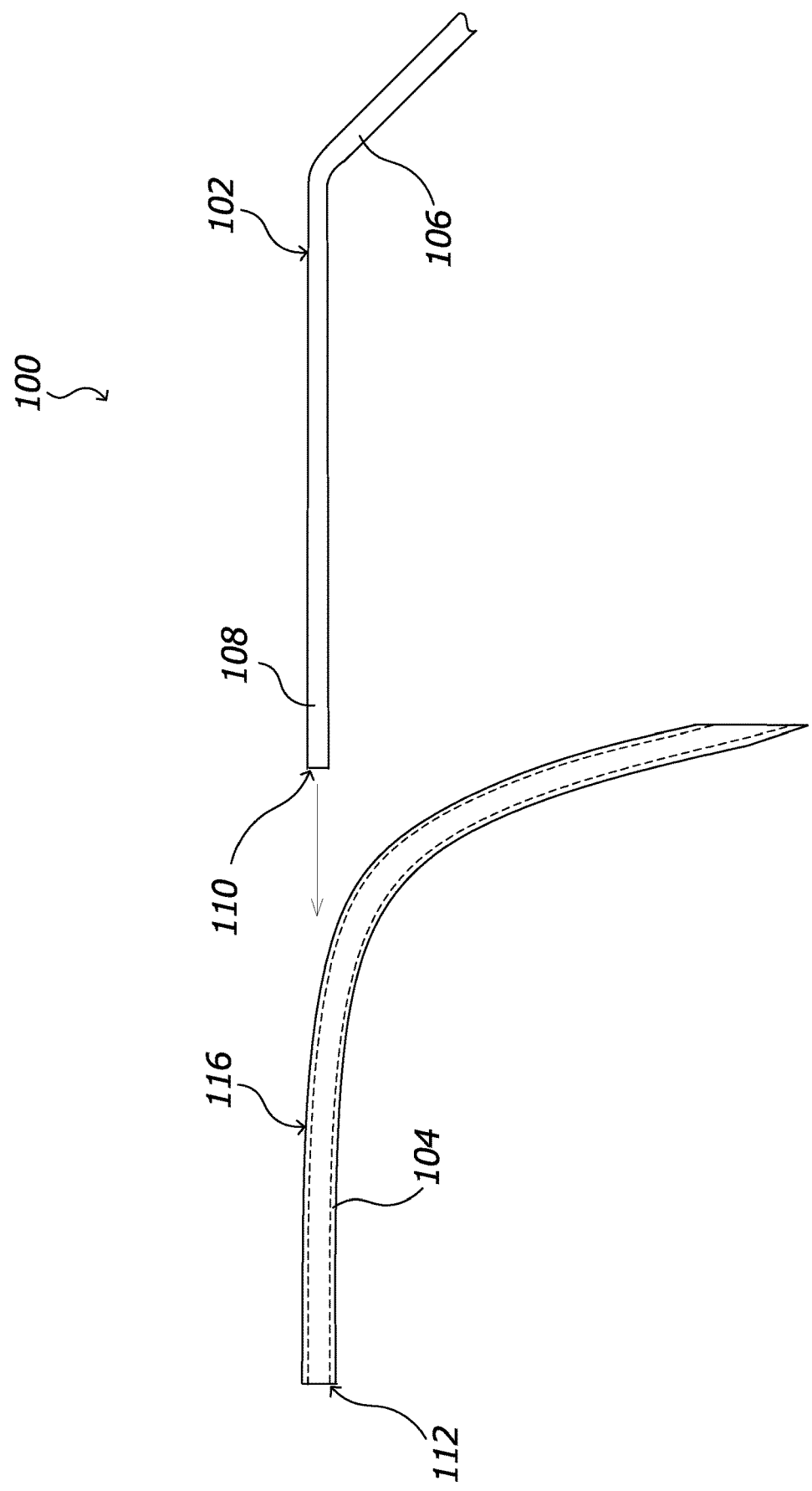
FIGS. 15*a*-15*b* are illustrations of the advantageous embodiment according to FIG. 1.
Figure 15B:
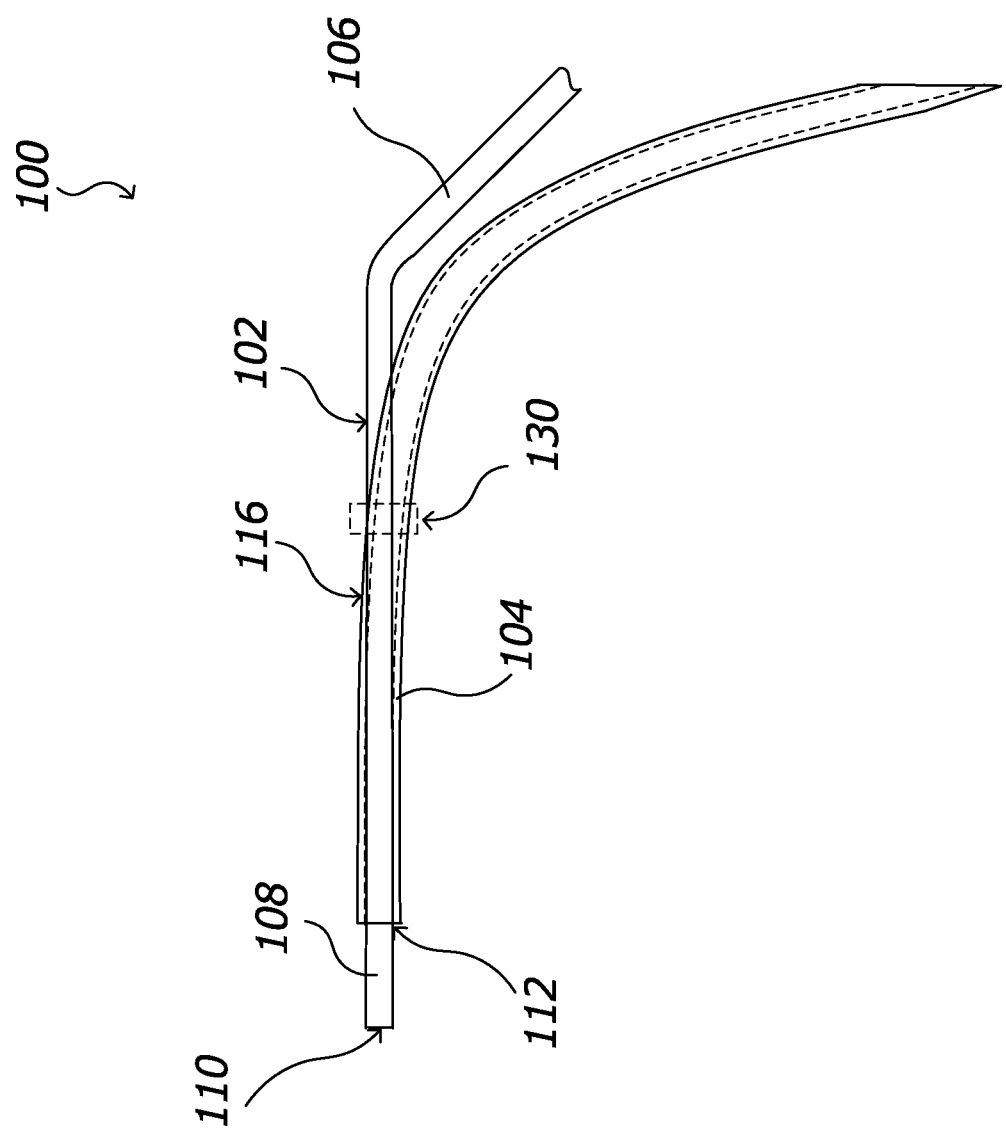

FIGS. 15a and 15b illustrate yet another embodiment of the present invention where the aspiration conduit 102 is removable from the sheath 116 enclosing the optical fibers 104. For example, FIG. 15a shows that the aspiration conduit 102 may be inserted (removable from) into the sheath 116 from a rear portion thereof. As shown in FIG. 15b, the aspiration conduit 102 is fully inserted into the sheath 116 and the tip 108 including distal end 110 extends a distance (d) from the ends 112 of the optical fibers 104. In this manner the optical system could be used, for example, with virtually any standard suction device and can be used with various sized suctions devices. Additionally, while the suction device may be disposable, the optical components could be sterilized and used multiple times.

It is further contemplated that the suction device may be "lockable" to engage with the optical components to vary the distance the ends of the optical fibers 104 are positioned from distal end 110. The locking mechanism 139 may comprise virtually any type of locking device, including, but not limited to, frictional fitting, a clamp, fitting, or the like.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A medical instrument for providing illuminating light generated by a light source to a cavity and aspiration of the cavity comprising:
    an aspiration pipe having a longitudinal length and having a sidewall defining a conduit and having an end face defining a distal most point of said pipe, said conduit having an opening positioned in the end face, the opening being coaxial with the conduit;
    said aspiration pipe adapted to be connected to an aspirator;
    an illumination path adapted to be connected at one end to the light source and to transmit illuminating light from the light source to the cavity, the illumination path extending from the light source to the medical instrument, said illumination path positioned about an exterior surface of said aspiration pipe and extending along the exterior surface for at least a portion of the longitudinal length of said aspiration pipe; and
    wherein the illuminating light transmitted along said illumination path is adapted to illuminate the cavity.

2. The medical instrument according to claim 1, wherein at least a portion of said illumination path comprises an optical fiber.

3. The medical instrument according to claim 2, wherein the optical fiber comprises a plurality of optical fibers.

4. The medical instrument according to claim 3, wherein at least a portion of said illumination path comprises a plastic material.

5. The medical instrument according to claim 4, wherein the plastic material comprises a transparent or translucent material adapted to allow the illuminating light to pass therethrough.

6. The medical instrument according to claim 4, wherein the plastic material that forms at least a portion of said illumination path comprises a tip of the aspiration pipe.

7. The medical instrument according to claim 1, wherein the light source comprises and LED.

8. The medical instrument according to claim 1, wherein said illumination path is positioned at least partially around the exterior surface of said aspiration pipe for a portion of the longitudinal length.

9. The medical instrument according to claim 1, further comprising a covering surrounding at least a portion of said aspiration pipe and said illumination path.

10. A medical instrument for providing illuminating light to and aspiration of a cavity comprising:
- an aspiration pipe having a longitudinal length and a sidewall defining a conduit and having an end face defining a distal most point of said pipe, said conduit having an opening positioned in the end face, the opening being coaxial with the conduit;
- said aspiration pipe adapted to be connected to an aspirator;
- an illumination path extending from a light source generating illuminating light to the cavity, said illumination path extending along an exterior of said aspiration pipe for at least a portion of the longitudinal length;
- said illumination path adapted to allow illuminating light from the light source to be transmitted to the cavity;
- wherein at least a portion of said illumination path comprises a plurality of optical fibers; and
- wherein at least a portion of said illumination path comprises a transparent or translucent plastic material.

11. The medical instrument according to claim 10, wherein the illumination path is configured such that:
(a) the illuminating light enters the plurality of optical fibers and is transmitted along of length of the optical fibers,
(b) the illuminating light exits the optical fibers,
(c) the illuminating light enters the transparent or translucent plastic material, and
(d) the illuminating light exits the transparent or translucent plastic material and illuminates the cavity.

12. The medical instrument according to claim 10, wherein said light source comprises and LED.

13. The medical instrument according to claim 10, further comprising a covering surrounding at least a portion of said aspiration pipe and said illumination path.

* * * * *